(12) United States Patent
Lee et al.

(10) Patent No.: US 12,702,785 B2
(45) Date of Patent: Aug. 11, 2026

(54) REHABILITATION ASSISTANT SYSTEM FOR PATIENT WITH COGNITIVE IMPAIRMENTS

(71) Applicants: ASIA UNIVERSITY, Taichung City (TW); METABRAIN TECHNOLOGY PTE. LTD., Singapore (SG)

(72) Inventors: Shin-Da Lee, Taichung (TW); Shang-Yu Yang, Taichung (TW); Chen-Chao Hsu, Taichung (TW); Ming-Jen Hsu, Taipei (TW)

(73) Assignees: ASIA UNIVERSITY, Taichung City (TW); METABRAIN TECHNOLOGY PTE. LTD., Singapore (SG)

( * ) Notice: Subject to any disclaimer, the term of this patent is extended or adjusted under 35 U.S.C. 154(b) by 1021 days.

(21) Appl. No.: 17/896,403

(22) Filed: Aug. 26, 2022

(65) Prior Publication Data

US 2023/0066293 A1 Mar. 2, 2023

(30) Foreign Application Priority Data

Aug. 27, 2021 (TW) ................................ 110131803

(51) Int. Cl.
*A61M 21/00* (2006.01)
*A61H 39/00* (2006.01)
(Continued)

(52) U.S. Cl.
CPC ............. *A61M 21/00* (2013.01); *A61H 39/00* (2013.01); *A63B 22/0605* (2013.01); *G06F 3/14* (2013.01);
(Continued)

(58) Field of Classification Search
CPC . A61M 21/00–02; A61N 5/0618–0619; A61H 39/00; G16H 20/40; A42B 1/017; A61B 5/16–18
See application file for complete search history.

(56) References Cited

U.S. PATENT DOCUMENTS

2004/0092859 A1* 5/2004 Schikora ................ A61H 39/00 604/20
2010/0248905 A1* 9/2010 Lu ...................... A63B 22/0605 482/57
(Continued)

*Primary Examiner* — Thaddeus B Cox
(74) *Attorney, Agent, or Firm* — MUNCY, GEISSLER, OLDS & LOWE, P.C.

(57) ABSTRACT

A rehabilitation assistant system for patients with cognitive impairments, including an audio stimulation unit, an acupoint stimulation unit, a phototherapeutic unit, an electronic stimulation unit, a display and optical frequency-flashed stimulation unit and a control unit. The audio stimulation unit broadcast a binaural beats with frequency following response, and the acupoint stimulation unit includes several acupoint agents to output physical stimulation to a user. The phototherapeutic unit includes two near-infrared light groups, and the electronic stimulation unit includes two electrical stimulation agents to output physical stimulation to the user. The display and optical frequency-flashed stimulation unit is switchable between a display mode and an optical frequency-flashed stimulation mode, and the control unit simultaneously controls the audio stimulation unit to broadcast the binaural beats with frequency following response so as to improve the rehabilitation efficiency in patients with cognitive impairment.

10 Claims, 10 Drawing Sheets

(51) Int. Cl.
*A63B 22/06* (2006.01)
*G06F 3/14* (2006.01)
*H04R 1/10* (2006.01)

(52) U.S. Cl.
CPC ......... *H04R 1/1008* (2013.01); *H04R 1/1041* (2013.01); *A61H 2039/005* (2013.01); *A61M 2021/0027* (2013.01); *A61M 2021/005* (2013.01); *A61M 2205/052* (2013.01); *A61M 2205/054* (2013.01); *A61M 2205/056* (2013.01)

(56) References Cited

U.S. PATENT DOCUMENTS

| | | | | |
|---|---|---|---|---|
| 2015/0005568 | A1* | 1/2015 | Chib | A61N 2/006 607/45 |
| 2019/0321258 | A1* | 10/2019 | Malik | A61N 1/0408 |
| 2020/0206567 | A1* | 7/2020 | Jung | A63B 23/0476 |
| 2020/0306536 | A1* | 10/2020 | Wang | A61H 1/00 |
| 2020/0382884 | A1* | 12/2020 | Chang | A61H 39/00 |
| 2022/0184398 | A1* | 6/2022 | Choi | A61N 1/36082 |
| 2023/0405261 | A1* | 12/2023 | Cimadamore | A61M 21/02 |

* cited by examiner

612(622)
25
2
22
222
611(621)
615(625)
615(625)
614(624)
613(623)
61(62)
26
26
63
6
631
631

Mini-Mental State Examination (MMSE)

Patient's Name: ______________________ Date: __________

*Instructions:* *Ask the questions in the order listed. Score one point for each correct response within each question or activity.*

| Maximum Score | Patient's Score | Questions |
|---|---|---|
| 5 | | "What is the year? Season? Date? Day of the week? Month?" |
| 5 | | "Where are we now: State? County? Town/city? Hospital? Floor?" |
| 3 | | The examiner names three unrelated objects clearly and slowly, then asks the patient to name all three of them. The patient's response is used for scoring. The examiner repeats them until patient learns all of them, if possible. Number of trials: ________ |
| 5 | | "I would like you to count backward from 100 by sevens." (93, 86, 79, 72, 65, ...) Stop after five answers.<br>Alternative: "Spell WORLD backwards." (D-L-R-O-W) |
| 3 | | "Earlier I told you the names of three things. Can you tell me what those were?" |
| 2 | | Show the patient two simple objects, such as a wristwatch and a pencil, and ask the patient to name them. |
| 1 | | "Repeat the phrase: 'No ifs, ands, or buts.'" |
| 3 | | "Take the paper in your right hand, fold it in half, and put it on the floor." (The examiner gives the patient a piece of blank paper.) |
| 1 | | "Please read this and do what it says." (Written instruction is "Close your eyes.") |
| 1 | | "Make up and write a sentence about anything." (This sentence must contain a noun and a verb.) |
| 1 | | "Please copy this picture." (The examiner gives the patient a blank piece of paper and asks him/her to draw the symbol below. All 10 angles must be present and two must intersect.) |
| 30 | | TOTAL |

(Adapted from Rovner & Folstein, 1987)

FIG. 8

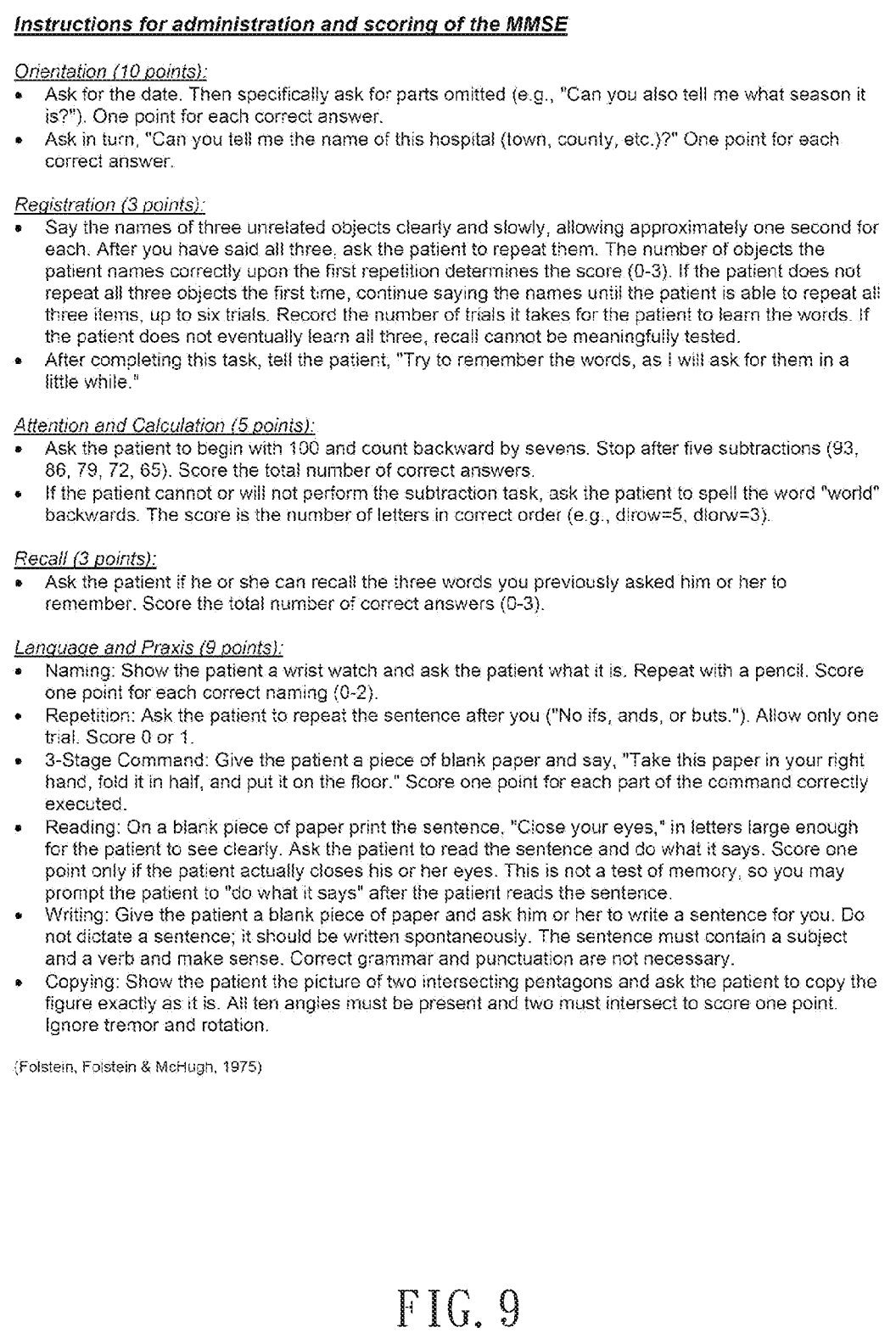

*Instructions for administration and scoring of the MMSE*

*Orientation (10 points):*

- Ask for the date. Then specifically ask for parts omitted (e.g., "Can you also tell me what season it is?"). One point for each correct answer.
- Ask in turn, "Can you tell me the name of this hospital (town, county, etc.)?" One point for each correct answer.

*Registration (3 points):*

- Say the names of three unrelated objects clearly and slowly, allowing approximately one second for each. After you have said all three, ask the patient to repeat them. The number of objects the patient names correctly upon the first repetition determines the score (0-3). If the patient does not repeat all three objects the first time, continue saying the names until the patient is able to repeat all three items, up to six trials. Record the number of trials it takes for the patient to learn the words. If the patient does not eventually learn all three, recall cannot be meaningfully tested.
- After completing this task, tell the patient, "Try to remember the words, as I will ask for them in a little while."

*Attention and Calculation (5 points):*

- Ask the patient to begin with 100 and count backward by sevens. Stop after five subtractions (93, 86, 79, 72, 65). Score the total number of correct answers.
- If the patient cannot or will not perform the subtraction task, ask the patient to spell the word "world" backwards. The score is the number of letters in correct order (e.g., dlrow=5, dlorw=3).

*Recall (3 points):*

- Ask the patient if he or she can recall the three words you previously asked him or her to remember. Score the total number of correct answers (0-3).

*Language and Praxis (9 points):*

- Naming: Show the patient a wrist watch and ask the patient what it is. Repeat with a pencil. Score one point for each correct naming (0-2).
- Repetition: Ask the patient to repeat the sentence after you ("No ifs, ands, or buts."). Allow only one trial. Score 0 or 1.
- 3-Stage Command: Give the patient a piece of blank paper and say, "Take this paper in your right hand, fold it in half, and put it on the floor." Score one point for each part of the command correctly executed.
- Reading: On a blank piece of paper print the sentence, "Close your eyes," in letters large enough for the patient to see clearly. Ask the patient to read the sentence and do what it says. Score one point only if the patient actually closes his or her eyes. This is not a test of memory, so you may prompt the patient to "do what it says" after the patient reads the sentence.
- Writing: Give the patient a blank piece of paper and ask him or her to write a sentence for you. Do not dictate a sentence; it should be written spontaneously. The sentence must contain a subject and a verb and make sense. Correct grammar and punctuation are not necessary.
- Copying: Show the patient the picture of two intersecting pentagons and ask the patient to copy the figure exactly as it is. All ten angles must be present and two must intersect to score one point. Ignore tremor and rotation.

(Folstein, Folstein & McHugh, 1975)

FIG. 9

*Interpretation of the MMSE*

| Method | Score | Interpretation |
|---|---|---|
| Single Cutoff | <24 | Abnormal |
| Range | <21 | Increased odds of dementia |
| | >25 | Decreased odds of dementia |
| Education | 21 | Abnormal for 8th grade education |
| | <23 | Abnormal for high school education |
| | <24 | Abnormal for college education |
| Severity | 24-30 | No cognitive impairment |
| | 18-23 | Mild cognitive impairment |
| | 0-17 | Severe cognitive impairment |

*Sources:*

- Crum RM, Anthony JC, Bassett SS, Folstein MF. Population-based norms for the mini-mental state examination by age and educational level. *JAMA*. 1993;269(18):2386-2391.
- Folstein MF, Folstein SE, McHugh PR. "Mini-mental state": a practical method for grading the cognitive state of patients for the clinician. *J Psychiatr Res*. 1975;12:189-198.
- Rovner BW, Folstein MF. Mini-mental state exam in clinical practice. *Hosp Pract*. 1987;22(1A):99, 103, 106, 110.
- Tombaugh TN, McIntyre NJ. The mini-mental state examination: a comprehensive review. *J Am Geriatr Soc*. 1992;40(9):922-935.

FIG. 10

REHABILITATION ASSISTANT SYSTEM FOR PATIENT WITH COGNITIVE IMPAIRMENTS

BACKGROUND OF THE INVENTION

Field of the Invention

The present invention relates to a rehabilitation assistant system, in particular to a rehabilitation assistant system for patient with cognitive impairments.

Description of the Prior Art

Since 2001, Taiwan's population over 65 years old has continued to grow. According to statistics, in 2018, there were 3.31 million people over 65 years old in Taiwan, accounting for 14% of the total population, officially entering the "elderly society" (Statistics Office of the Ministry of the Interior, 2018), in which the elderly people with Mild Cognitive Impairment (MCI) accounted for 18.32%. As the number of elderly people in Taiwan increases year by year, it is expected that the number of elderly people with mild cognitive impairment will also increase rapidly.

Mild cognitive impairment is defined as the degree of cognitive decline of a case far exceeds the age and education level at this stage, and it is usually in the transition period between the normal elderly and the process of dementia. But unlike dementia, the elderly people with mild cognitive impairment are not affected in basic activities of daily living (BADL), but their cognitive impairment is affected in instrumental activities of daily living (IADL).

The elderly people with mild cognitive impairment are the first to lose their instrumental activities of daily living, and the functional defects that occur are common such as financial management and telephone use. The instrumental activities of daily living require more complex cognitive abilities than the basic activities of daily living. Therefore, when the cognitive function declines rapidly, there is a high risk of turning into dementia in the future, such as Alzheimer's disease in dementia. In addition, previous studies have pointed out that instrumental activities of daily living are highly correlated with cognitive abilities such as memory and processing complex tasks. In other words, the elderly people with mild cognitive impairment are prone to impairment of cognitive and instrumental activities of daily living. Therefore, it is very important for the elderly with mild cognitive impairment to find an intervention way to maintain their cognitive and instrumental activities of daily living.

SUMMARY OF THE INVENTION

Therefore, it is an object of the present invention to provide a rehabilitation assistant system for patient with cognitive impairments.

Therefore, the rehabilitation assistant system for patient with cognitive impairments of the present invention is used by a user. The rehabilitation assistant system for patient with cognitive impairments includes a supporting unit, an audio stimulation unit, an acupoint stimulation unit, a phototherapeutic unit, an electronic stimulation unit, a display and optical frequency-flashed stimulation unit, an exercise unit, and a control unit.

The supporting unit corresponds to the head shape of the user, and includes two ears corresponding to both ears of the user, a top-side portion that spans the top of the user's head upward, a back-side portion that is connected between the ear portions and spans the back of the user's back skull, a front-side portion connected between the ears and spanning the user forward, and the top-side portion has a top areas located at the center of the ears, and two side areas respectively connected between the ears and the top areas; the audio stimulation unit includes two loudspeakers arranged at the ears, and the loudspeakers are used to broadcast a binaural beats with frequency following response to both ears of the user, and the binaural beats with frequency following response has an audio frequency difference; the acupoint stimulation unit includes an acupoint setting base arranged in the top area, and several acupoint agents, which are used to output physical stimulation of laser light to the user's head acupoints; one of the acupoint agents is adjustably set on the acupoint setting base at the center of the top area to correspond to Baihui acupoint of the user; one of the acupoint agents can be positioned at the acupoint setting base in a position-adjustable manner at 4.5 times of one finger distance forward from the center of the top area, corresponding to the Shenting acupoint of the user; two of the acupoint agents can be positioned at the back-side portion in a position-adjustable manner and located at the center of the top area by seven times the finger distance backward, and are separated by 2.25 times of the finger distance in the direction of the ears to respectively correspond to two Fengchi acupoints of users; the finger distance is substantially 2.3 cm; this phototherapeutic unit includes two near-infrared light lamp groups for emitting low-energy near-infrared light, wherein a near-infrared light lamp group is arranged on this acupoint setting base and surrounds the corresponding Baihui acupoint, the acupoint agents, wherein another near-infrared light lamp group is disposed on the acupoint setting base and surrounds the acupoint agents corresponding to the Shenting acupoint; the electronic stimulation unit includes a first setting base and a second setting base that are respectively arranged in the side areas, and two are respectively arranged in the first setting base and the electronical stimulation agents of the second setting base, the electronical stimulation agents is used to output physical stimulation to the user's head, and the electronical stimulation agents corresponds to the position of the international 10-20 system of electrode placement respectively in the F3 position and the F4 position; the display and optical frequency-flashed stimulation unit are arranged on the supporting unit and can be switched between a display mode and an optical frequency-flashed stimulation mode, during the display mode, the display and optical frequency-flashed stimulation unit display a virtual image for the user's two eyes to watch, in the optical frequency-flashed stimulation mode, the display and optical frequency-flashed stimulation unit stimulates the user's two eyes with a flickering flashlight; the control unit is electrically connected to the loudspeakers, the acupoint agents, the near-infrared light lamp groups, the electronical stimulation agents, and the display and optical frequency-flashed stimulation unit, and stores the digital information of the beat frequency music, and according to a preset command, can be simultaneously controlled the loudspeakers to broadcast the binaural beats with frequency following response, the acupoint agents to emit physical stimulation, the near-infrared light group to emit near-infrared light, the electronical stimulation agents to emit physical stimulation, and the display and optical frequency-flashed stimulation unit to switch modes.

The effect of the present invention is: by setting the loudspeakers, the acupoint agents, the near-infrared light lamp group, the electronical stimulation agents, the display and light frequency stimulation unit and the exercise unit, the use of patients can obtain multiple stimulations in a single course of treatment at the same time, and improve the rehabilitation efficiency of patients with cognitive impairment.

BRIEF DESCRIPTION OF THE DRAWINGS

Other features and effects of the present invention will appear clearly in the embodiments with reference to the drawings, in which:

FIG. 8 is a schematic diagram of the front half of an existing assessment sheet;

FIG. 9 is a schematic diagram of the second half of the existing assessment sheet;

FIG. 10 is a schematic diagram of the interpretation of the MMSE of the existing assessment sheet.

DETAILED DESCRIPTION OF THE PREFERRED EMBODIMENTS

Figure 1:
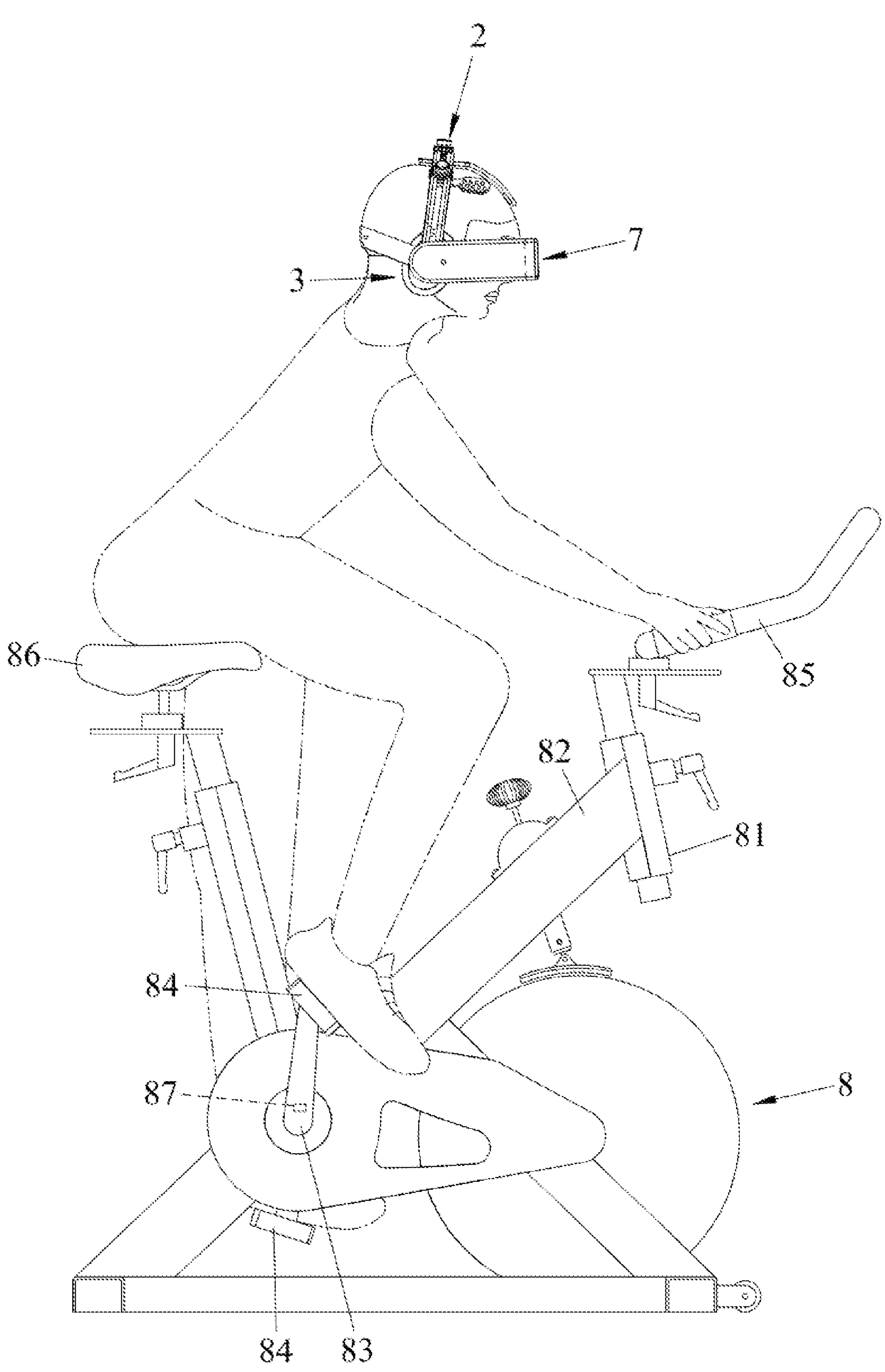
FIG. 1 is a perspective view of an embodiment of the rehabilitation assistant system for cognitive impairment of the present invention.
Figure 2:
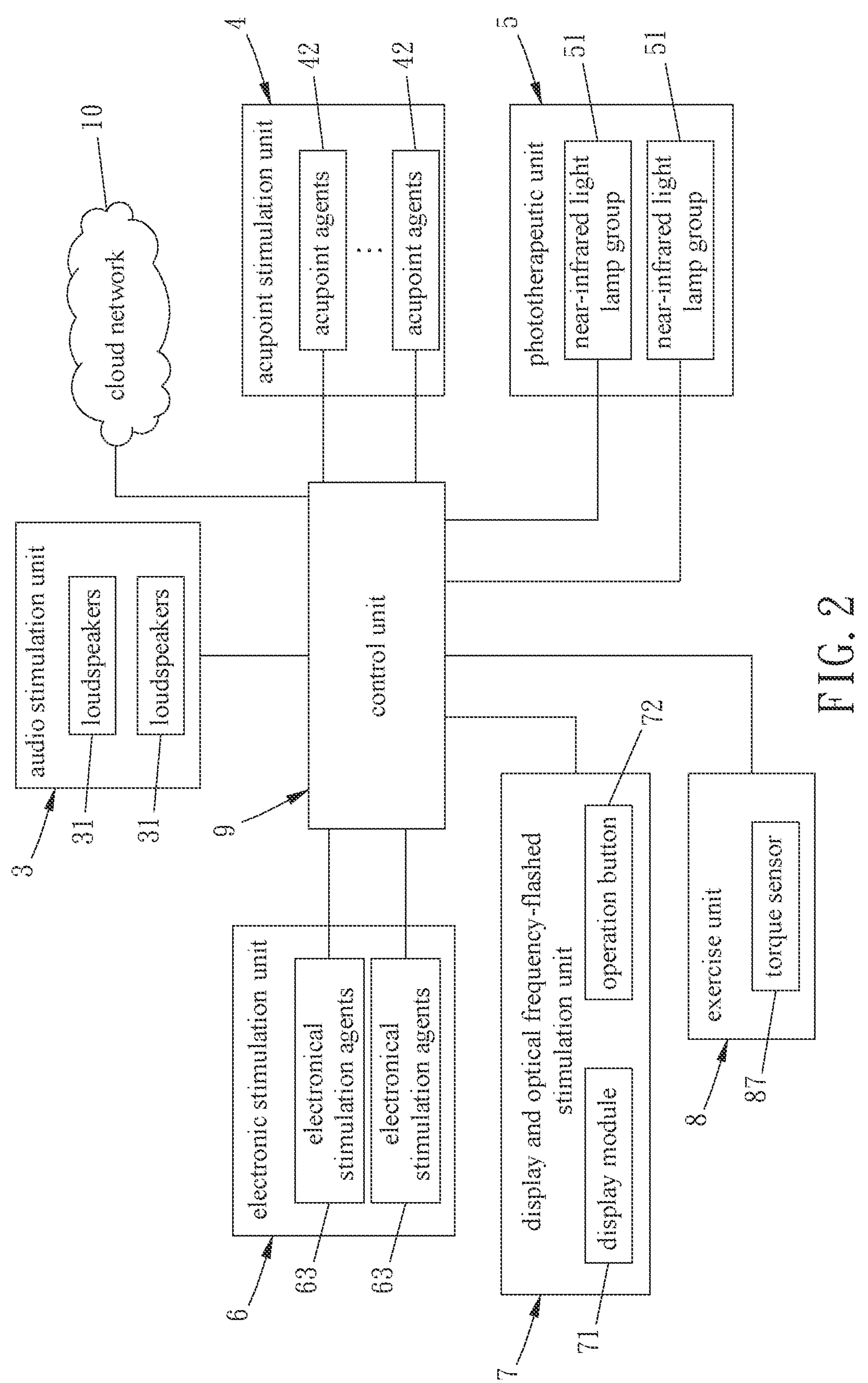
FIG. 2 is a system block diagram of the embodiment and a cloud network.
Figure 3:
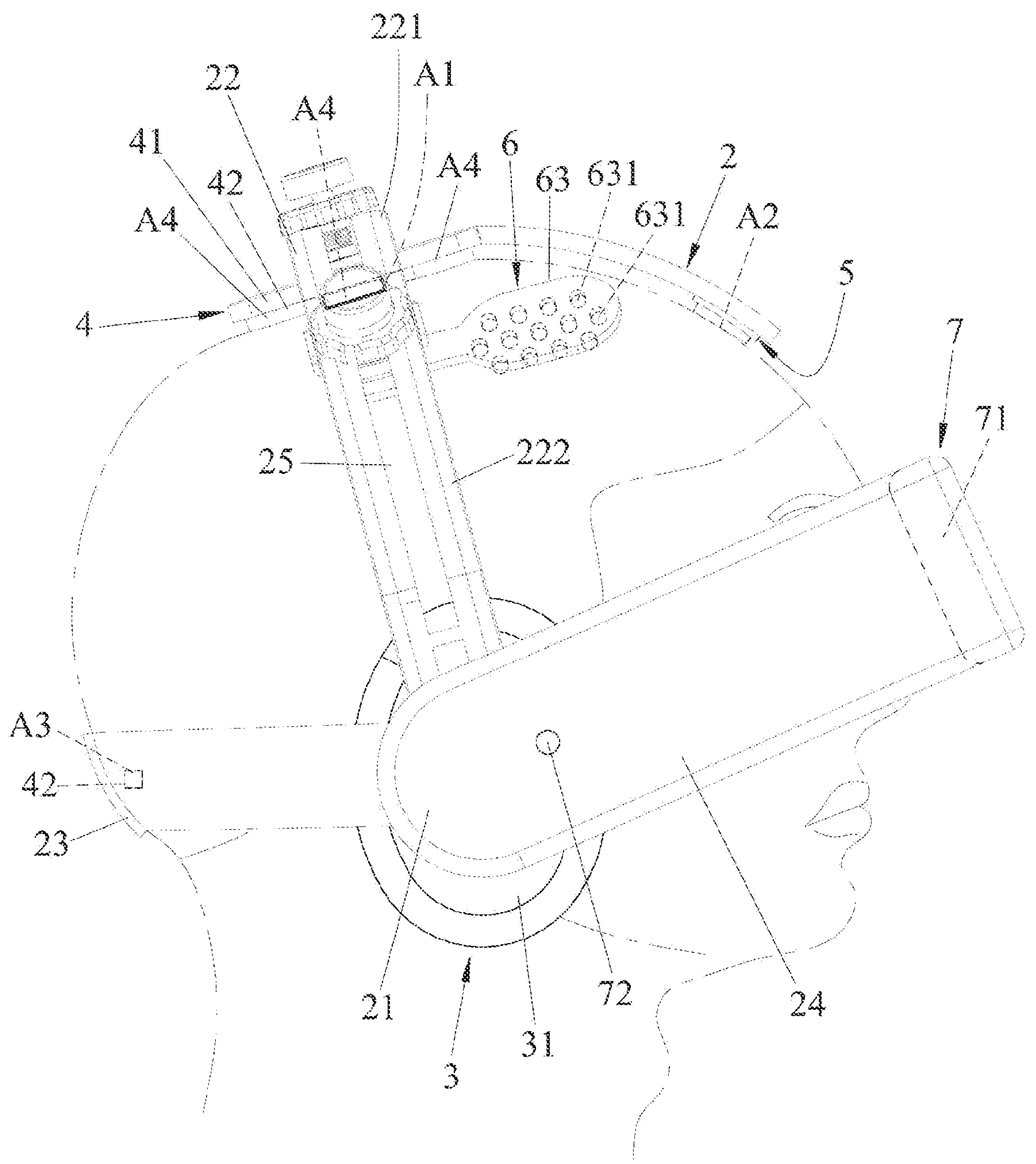
FIG. 3 is an incomplete side view of this embodiment.

Referring to FIGS. 1, 2 and 3, an embodiment of the rehabilitation assistant system for patient with cognitive impairments of the present invention is used for a user. The rehabilitation assistant system for patient with cognitive impairments includes a supporting unit 2, an audio stimulation unit 3, an acupoint stimulation unit 4, a phototherapeutic unit 5, an electronic stimulation unit 6, a display and optical frequency-flashed stimulation unit 7, an exercise unit 8, and a control unit 9.

Figure 4:
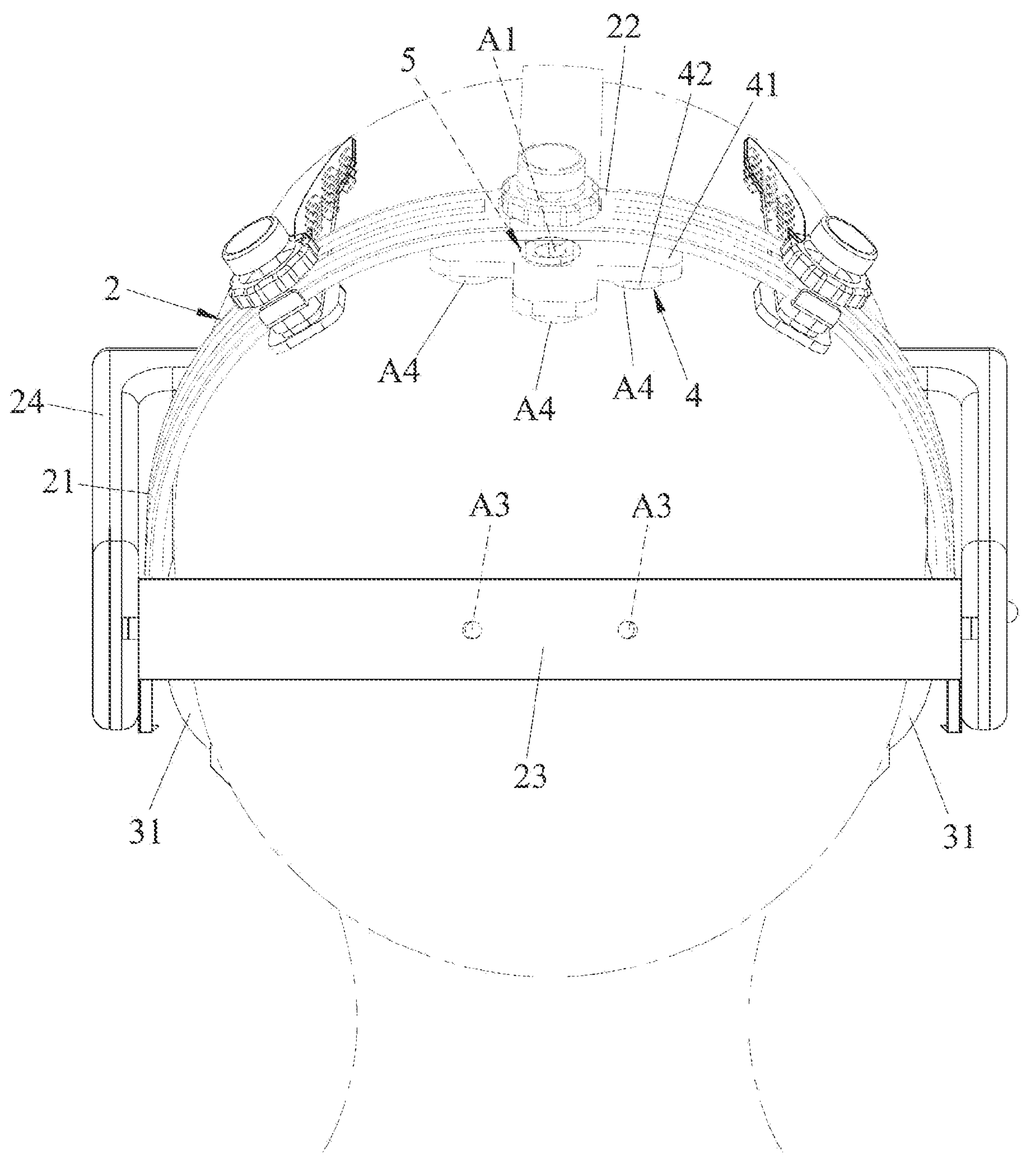
FIG. 4 is an incomplete rear view of this embodiment.
Figure 5:
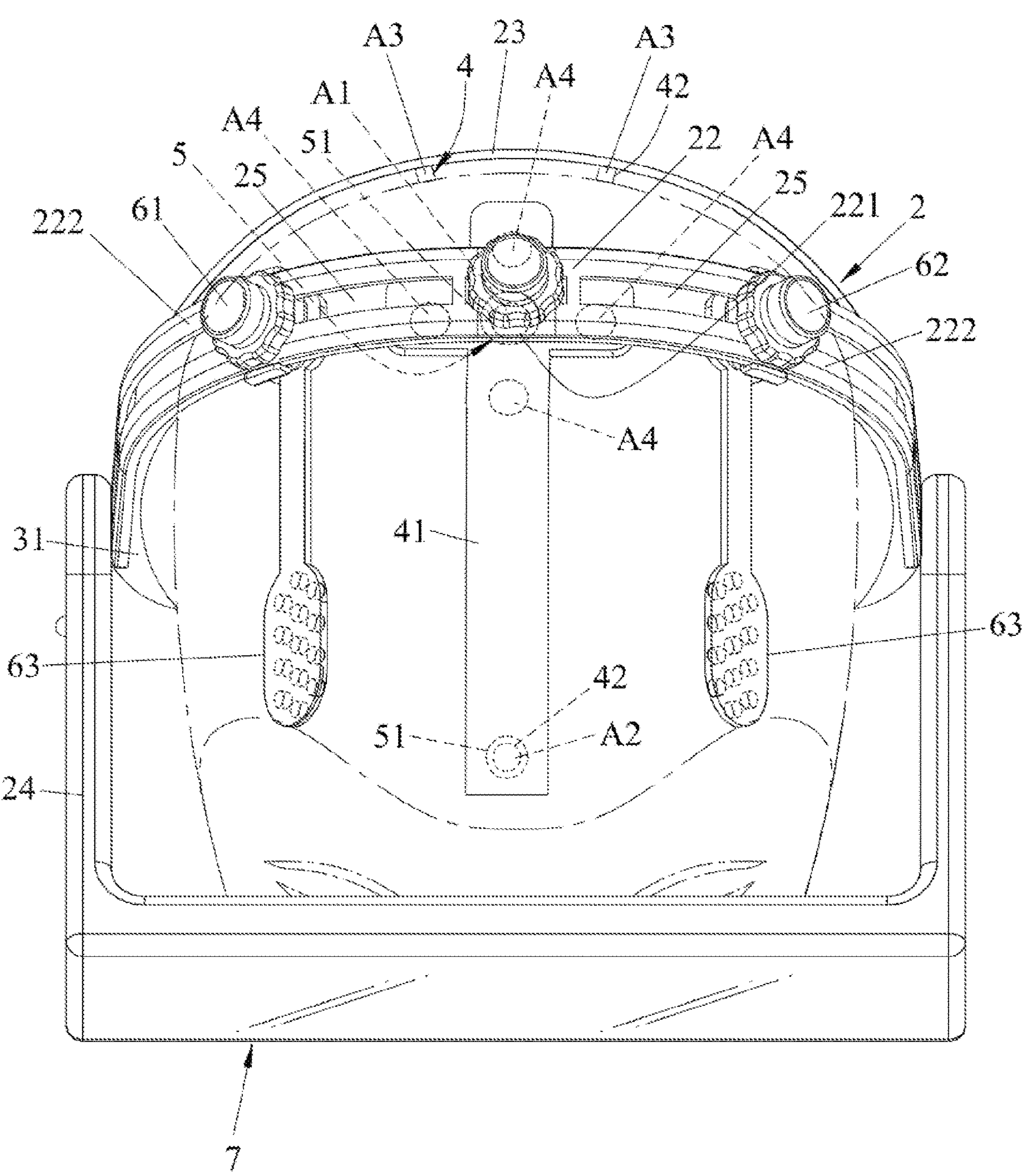
FIG. 5 is an incomplete plan view of this embodiment.

Referring to FIGS. 3, 4, and 5, the supporting unit 2 corresponds to the head shape of the user, and includes two ears 21 corresponding to both ears of the user, and one is connected between the ears 21. a top-side portion 22 that spans the top of the user's head upward, a back-side portion that is connected between the ear portions and spans the back of the user's back skull, a front-side portion 24 connected between the ears 21 and spanning the user forward, the two mounting slots 25, and several conductive strips 26 (see FIG. 6) are arranged at the bottom of the top-side portion 22, and the top-side portion 22 has a top areas 221 located at the center of the ears 21, two side areas 222 respectively connected between the ears 21 and the top areas 221, and the mounting slots 25 are located in the side areas 222 respectively.

The audio stimulation unit 3 includes two loudspeakers 31 arranged at the ears 21, and the loudspeakers 31 are used to broadcast a binaural beats with frequency following response (Binaural beats with frequency following response) to both ears of the user, and the binaural beats with frequency following response has an audio frequency difference. In this embodiment, the audio frequency difference of the beat music is between 0.1 Hz and 45 Hz.

The acupoint stimulation unit 4 includes an acupoint setting base 41 arranged in the top area 221, and several acupoint agents 42, which are used to output physical stimulation of laser light to the user's head acupoints. In this embodiment, the laser light wavelength of the acupoint agents 42 ranges from 500 nm to 900 nm, and the output power ranges from 100 MW to 200 MW.

One of the acupoint agents 42 is adjustably set on the acupoint setting base 41 at the center of the top area 221 to correspond to Baihui acupoint (international acupoint code GV20) of the user, which is indicated by the number A1 in the figure.

One of the acupoint agents 42 can be positioned at the acupoint setting base 41 in a position-adjustable manner at 4.5 times of one finger distance forward from the center of the top area 221, corresponding to the Shenting acupoint (international acupoint code GV24) of the user, which is indicated by the number A2 in the figure. In this embodiment, the finger distance is substantially 2.3 cm.

Two of the acupoint agents 42 can be positioned at the back-side portion 23 in a position-adjustable manner and located at the center of the top area 221 by seven times the finger distance backward, and are separated by 2.25 times of the finger distance in the direction of the ears 21 to respectively correspond to two Fengchi acupoints (international acupoint code GB20) of users, which are indicated by the number A3 in the figure.

Four of the acupoint agents 42 can be positioned at the acupoint setting base 41 in a position-adjustable manner and spaced apart from the center of the top area 221 by the finger distance respectively correspond to the four Sishencong acupoints (international acupoint code EX-HN1) of the user, which are indicated by the number A4 in the figure.

It should be noted that the aforementioned method of corresponding to the user's acupoints can measure the resistance of human skin near the acupoints, and take the lowest resistance as the position of the acupoints, and then fine-tune to make the corresponding acupoint agents 42 to correspond to the positions to complete the positioning of the acupoints.

This phototherapeutic unit 5 includes two near-infrared light lamp groups 51 for emitting low-energy near-infrared light, wherein a near-infrared light lamp group 51 is arranged on this acupoint setting base 41 and surrounds the corresponding Baihui point A1. The acupoint agents 42, wherein another near-infrared light lamp group 51 is disposed on the acupoint setting base 41 and surrounds the acupoint agents 42 corresponding to the Shenting acupoint A2. In this embodiment, the wavelengths of the light emitted by the near-infrared light sets 51 are between 760 and 860 nm, preferably 810 nm, and the pulse frequency is 10 Hz.

Figure 6:
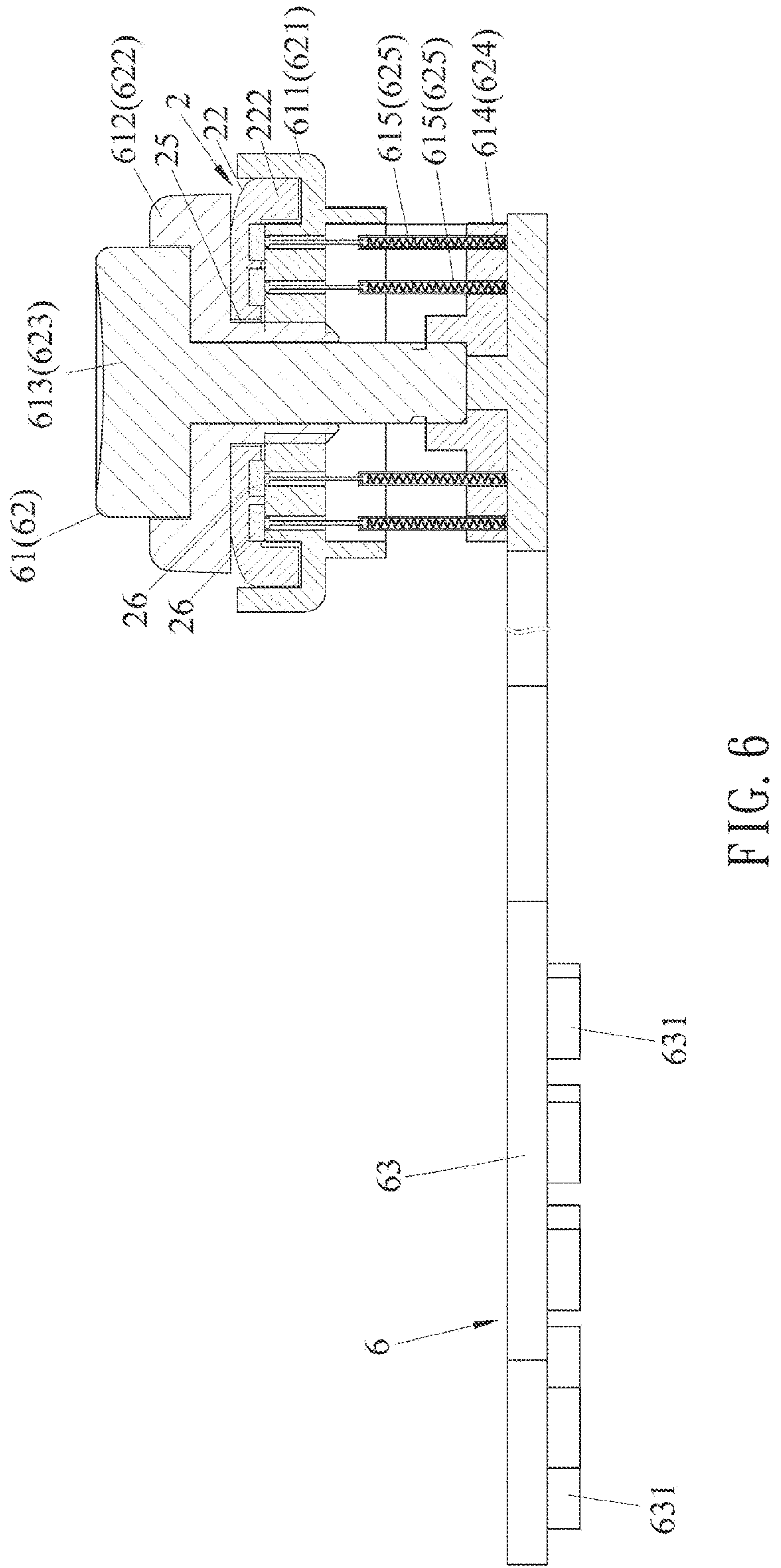
FIG. 6 is an incomplete sectional schematic diagram of a bracket unit and an electronic stimulation unit of this embodiment.

Referring to FIGS. 3, 5, and 6, the electronic stimulation unit 6 includes a first setting base 61 and a second setting base 62 that are respectively arranged in the side areas 222, and two are respectively arranged in the first setting base 61 and the electronical stimulation agents 63 of the second setting base 62, the electronical stimulation agents 63 is used to output physical stimulation to the user's head, and the electronical stimulation agents 63 corresponds to the position of the international 10-20 system of electrode placement respectively in the F3 position and the F4 position. In this embodiment, the physical stimulation is direct current for transcranial direct current stimulation (tDCS), the current size is between 0.5 mA and 2 mA, and the current density is between 0.03 mA/cm$^2$ and 0.09 mA/cm$^2$, but not limited to this, it can also be an electromagnetic pulse for transcranial magnetic stimulation (TMS), the electromagnetic frequency is between 1-20 Hz, the stimulation intensity is 90% aMT (active motor threshold), 120% rMT (rest motor threshold), where aMT and rMT are the regular intensity definitions of the transcranial magnetic stimulation instrument, so this manual will not describe them further.

The first setting base 61 has a first sliding member 611 disposed under one of the side areas 222 and the conductive strips 26, a first screw locking member 612 that passes through the respective mounting slots 25 from the side opposite to the first sliding member 611 of the top-side portion 22 and is screwed to the first sliding member 611 for fixing the first sliding member 611, A first positioning member 613 of the first sliding member 611 slidably passes through the first screw locking member 612 from the opposite side of the first locking screw locking member 612, a first mounting platform 614 arranged on the opposite side of the first sliding member 611 to the top-side portion 22 and screwed to the first positioning member 613, and several first conductive members 615 telescopically passing through the first sliding member 611 and the first mounting platform 614 and electrically connecting the conductive strips 26 respectively. One of the electronical stimulation agents 63 is disposed on the side of the first mounting platform 614 opposite to the top-side portion 22 and electrically connected to the first conductive members 615.

The second setting base 62 has a second sliding member 621 disposed under the other one of the side areas 222 and the conductive strips 26, a second screw locking member 622 passing through the respective mounting slots 25 from the side opposite to the top-side 22 and screwed to the second sliding member 621 for fixing the second sliding member 621, A second positioning member 623 of the second sliding piece 621 slidably passes through the second screw locking member 622 from the side opposite to the second screw locking member 622, a second mounting platform 624 arranged on the side opposite to the top-side portion 22 of the second sliding member 621 and screwed to the second positioning member 623, and several second conductive members telescopically passing through the second sliding member 621 and the second mounting platform 624 and electrically connecting the conductive strips 26 respectively. The other of the electronical stimulation agents 63 is disposed on the side of the second mounting platform 623 opposite to the top-side portion 22 and electrically connected to the second conductive members 625.

Each electronical stimulation agents 63 has several conductive pillars 631 arranged in parallel to output physical stimulation.

The display and optical frequency-flashed stimulation unit 7 are arranged on the supporting unit 2 and can be switched between a display mode and an optical frequency-flashed stimulation mode. During the display mode, the display and optical frequency-flashed stimulation unit display a virtual image (not shown) for the user's two eyes to watch, in the optical frequency-flashed stimulation mode, the display and optical frequency-flashed stimulation unit 7 stimulates the user's two eyes with a flickering flashlight. In this embodiment, the display and optical frequency-flashed stimulation unit 7 is a virtual image manipulation device, and includes a display module 71 and an operation button 72.

When the display and optical frequency-flashed stimulation unit 7 are in the optical frequency-flashed stimulation mode, the flickering flashlight displayed by the display and optical frequency-flashed stimulation unit 7 can blink at a predetermined frequency or stimulate the eyes of the user with an optical frequency difference, respectively. In this embodiment, the predetermined frequency is between 35 Hz and 45 Hz, so that the entire screen flashes at the same frequency, and when the user's eyes are stimulated respectively with the optical frequency difference, the user's double Eyes are stimulated by light of different frequencies.

Referring to FIGS. 1, 2, and 5, the exercise unit 8 is connected to the control unit 9 by a signal for the user to operate to exercise, the exercise unit 8 includes an exercise bike 81, and the exercise bike 81 has a frame 82, a crank 83 rotatably arranged on the frame 82, two pedals 84 arranged on opposite sides of the crank 83, a handle frame 85 and a seat 86 disposed on the frame 82, and a crank 83 is also signally connected to the control unit 9 to output a torque sensor 87 corresponding to the torque sensor 87 for measuring the torque of the crank 83.

The control unit 9 is electrically connected to the loudspeakers 31, the acupoint agents 42, the near-infrared light lamp groups 51, the electronical stimulation agents 63, and the display and optical frequency-flashed stimulation unit 7, and stores the digital information of the beat frequency music, and according to a preset command, can be simultaneously controlled the loudspeakers 31 to broadcast the binaural beats with frequency following response, the acupoint agents 42 to emit physical stimulation, the near-infrared light group 51 to emit near-infrared light, the electronical stimulation agents 63 to emit physical stimulation, and the display and optical frequency-flashed stimulation unit 7 to switch modes. In this embodiment, the control unit 9 is a personal computer.

Figure 7:
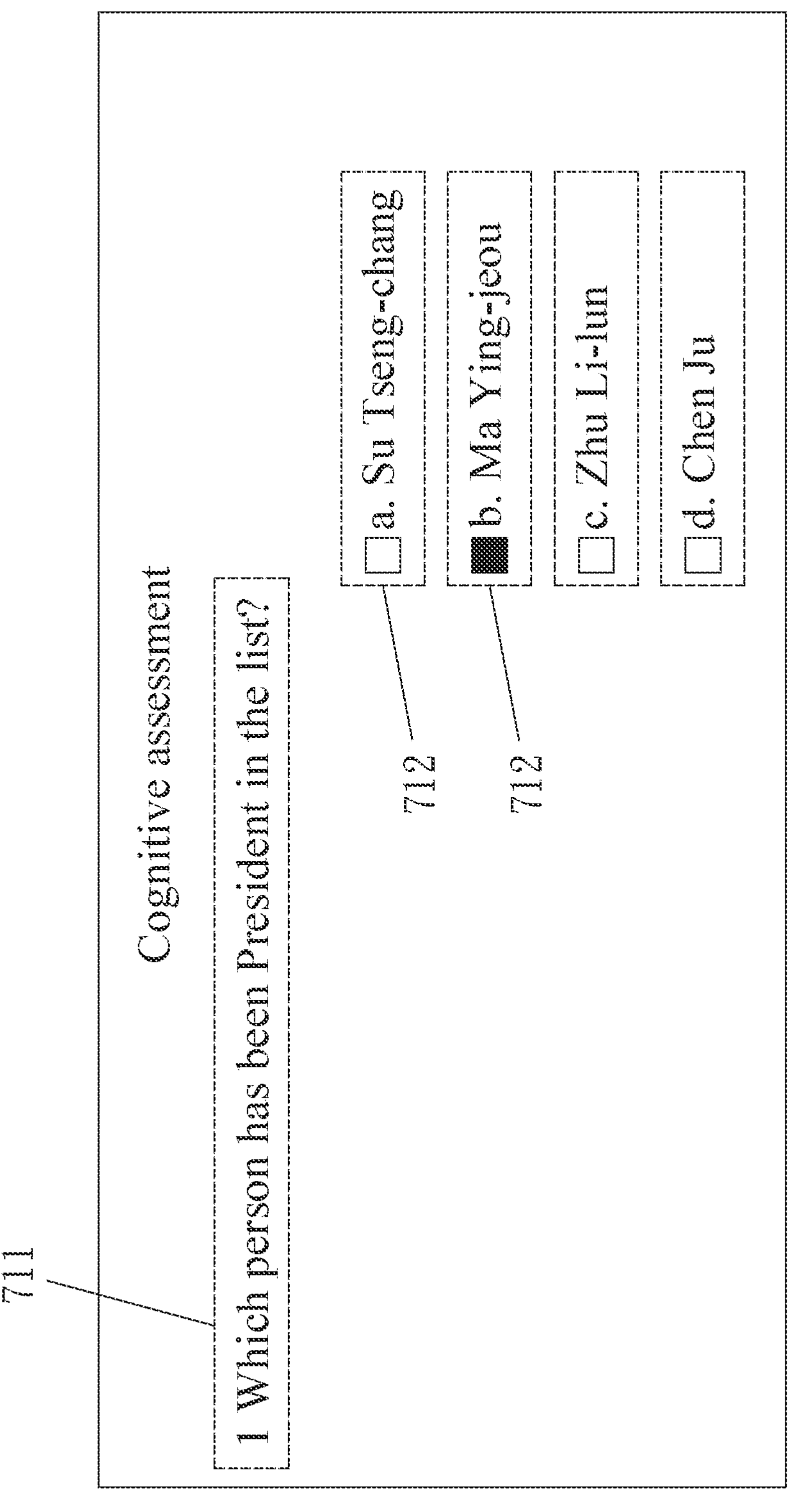
FIG. 7 is a schematic diagram of a screen displayed when the embodiment executes an assessment program.

Referring to FIGS. 2, 3, and 7, the control unit 9 can execute an assessment program, in which the control unit 9 controls the display module 71 to sequentially display several cognitions for evaluating cognitive impairment self-assessment questions 711, each cognitive self-assessment question 711 has several self-assessment options 712, and the selected self-assessment option 712 can be changed by changing the direction of the display module 71, and after confirmation through the operation button 72, a cognitive self-assessment score corresponding to the selected self-assessment option 712 is generated and stored, and after all the cognitive self-assessment questions 711 are answered, a cognitive result score is generated and stored after adding up all the cognitive self-assessment scores. In this embodiment, the display module 71 displays a set of cognitive self-assessment questions 711 at a time, and after the corresponding self-assessment option 712 is selected, the next group of cognitive self-assessment questions 711 is performed, but not limited to this, and in other implementations, multiple groups of cognitive self-assessment questions 711 may be displayed at the same time, and the source of these depression self-assessment questions 711 may be from the existing assessment sheets as shown in FIGS. 8, 9 and 10, but not limited to this.

Referring to FIGS. 1, 2 and 5, the control unit 9 can display a prompt message in the virtual image through the display and optical frequency-flashed stimulation unit 7 after the exercise unit 8 operates for a predetermined time. In this embodiment, the virtual image is a VR image, and the digital information and the preset command are downloaded through the cloud network 10 and pre-stored in the control unit 9.

When in use, the user wears the rehabilitation assistant system for patient with cognitive impairments first, and then the control unit 9 controls the speakers 31 to broadcast the beat music, causes the acupoint agents 42 to emit physical stimulation to the corresponding acupuncture points, causes the near-infrared light groups 51 to irradiate, and causes the electronical stimulation agents 63 to emit physical stimulation to the corresponding brain regions, so that the user can receive the beat music, the acupuncture points and the acupuncture points at the same time.

In addition, the user can perform the assessment program before use to obtain the pre-operation cognitive result score, and then perform the evaluation program again after the whole operation process to obtain the post-operation cognitive result score. The improvement degree of cognitive impairment can be seen from the two cognitive result scores, which can be used as a record and as a driving force for the user to further use.

Supplementary explanation is, in this case, the test results of the physical stimulation of the acupoint agents 42, the binaural beats with frequency following response, the near-infrared light groups 51 and the electronical stimulation agents 63 have been proved by the following references, so this specification will not further explain it.

1. Kim, H., Kim, H. K., Kim, S. Y, Kim, Y. I., Yoo, H. R., & Jung, I. C. (2019). Cognitive improvement effects of electro-acupuncture for the treatment of MCI compared with Western medications: a systematic review and Meta-analysis. BMC complementary and alternative medicine, 19(1), 13.
2. Chaieb, L., Wilpert, E. C., Reber, T. P., & Fell, J. (2015). Auditory beat stimulation and its effects on cognition and mood states. Frontiers in psychiatry, 6, 70.
3. Jirakittayakorn, N., & Wongsawat, Y. (2017). Brain responses to 40-Hz binaural beat and effects on emotion and memory. International Journal of Psychophysiology,
4. Barrett, D. W., & Gonzalez-Lima, F. (2013). Transcranial infrared laser stimulation produces beneficial cognitive and emotional effects in humans. Neuroscience, 230, 13-23.
5. Saltmarche A E, et al, Significant Improvement in Cognition in Mild to Moderately Severe Dementia Cases Treated with Transcranial Plus Intranasal Photobiomodulation: Case Series Report. Photomed Laser Surg. 2017 August; 35(8): 432-441.
6. F. Gonzalez-Lima and Douglas W. Barrett, Augmentation of cognitive brain functions with transcranial lasers, Front Syst Neurosci. 2014; 8:36.
7. Michael R Hamblin, Mechanisms and applications of the anti-inflammatory effects of photobiomodulation, AIMS Biophys. 2017; 4(3): 337-361.

In addition to providing the user with the binaural beats with frequency following response, the acupuncture points, low-energy irradiation and stimulation of the brain regions, the control unit 9 can also control the display and optical frequency-flashed stimulation unit 7 to display a designed virtual image in the display mode, which can be eight aspects of functional activities of daily living (cooking, shopping, going out, housework maintenance, washing clothes, making phone calls, taking drugs, etc. It should be noted that, since the content presented by this virtual image is not the technology to be protected in this case, this specification will not further explain it.

The control unit 9 can also control the display and optical frequency-flashed stimulation unit 7 to switch to the optical frequency-flashed stimulation mode, and in the optical frequency-flashed stimulation mode, stimulate the user's eyes with flickering flashlight, thereby improving cognition disorder. It should be noted that, according to the literature research of Iaccarino, H. F., Singer, A. C., Martorell, A. J., Rudenko, A., Gao, F., Gillingham, T. Z., . . . & Adaikkan, C. (2016). Gamma frequency entrainment attenuates amyloid load and modifies microglia. Nature, 540(7632), 230-235. and Garza, K. M., Zhang, L., Borron, B., Wood, L. B., & Singer, A. C. (2020). Gamma Visual Stimulation Induces a Neuroimmune Signaling Profile Distinct from Acute Neuroinflammation. Journal of Neuroscience, 40(6), 1211-1225. 40 Hz light-flickering (40 Hz light-flickering paradigm) irradiation can effectively reduce the concentration of β-amyloid protein and the deposited plaques in the visual cortex of mice, and it can be used as proof that it can improve the dysfunction of the nervous immune system.

In addition, the user can further ride the exercise bike 81 for exercise, which can improve cognitive disorder. According to the literature research of Tsai, C. L., Pai, M. C., Ukropec, J., & Ukropcová, B. (2019). Distinctive effects of aerobic and resistance exercise modes on neurocognitive and biochemical changes in individuals with mild cognitive impairment. Current Alzheimer Research, 16(4), 316-332. Tsai, C. L., Sun, H., Kuo, Y M., & Pai, M. C. (2019). The Role of Physical Fitness in Cognitive-Related Biomarkers in Persons at Genetic Risk of Familial Alzheimer's Disease. Journal of clinical medicine, 8(10), 1639. And the Role of Physical Fitness in Cognitive-Related Biomarkers in Persons at Genetic Risk of Familial Alzheimer's Disease. Journal of clinical medicine, 8(10), 1639. Regular aerobic exercise can improve the neurocognitive performance of the elderly with mild cognitive impairment, and aerobic exercise can significantly improve the concentrations of neurotrophic factors and inflammatory indicators of the people with mild cognitive impairment related to dementia, and promote neurocognitive performance, which can be used as a proof that exercise can improve the dysfunction of neuroimmune system.

The display and optical frequency-flashed stimulation unit 7 can display the movement status according to the feedback of the torque sensor 87, and can know the movement progress by displaying the prompt message and sounding the prompt sound through the speakers 31, which can improve the user's convenience.

To sum up, by arranging the loudspeakers 31, the acupoint agents 42, the near-infrared light groups 51, the electric stimulation agents 63, the display and optical frequency-flashed stimulation unit 7 and the exercise unit 8, the user can obtain multiple stimuli in a single course of treatment at the same time, and the rehabilitation efficiency of patients with cognitive impairment can be improved, so the purpose of the present invention can indeed be achieved.

However, the above are only examples of the present invention. While the scope of the present invention cannot be limited by this, all simple and equivalent changes and modifications made according to the patent application scope and the contents of the patent specification of the present invention are still within the scope of the present invention.

What is claimed is:

1. A rehabilitation assistant system for a patient with cognitive impairments, which is used by the patient, wherein the system includes:

a supporting unit that corresponds to a head shape of the patient, and that includes two ear portions corresponding to both ears of the patient, a top-side portion that spans a top of a head of the patient upward, a back-side portion that is connected between the ear portions and spans a back portion of a skull of the patient, a front-side portion connected between the ear portions and spanning a front portion of the skull of the patient, and the top-side portion has a top area located at a center of the ear portions, and two side areas respectively connected between the ear portions and the top area;

an audio stimulation unit that includes two loudspeakers arranged at the ear portions, and the loudspeakers are used to broadcast binaural beats to the both ears of the patient;

an acupoint stimulation unit that includes an acupoint setting base arranged in the top area, and acupoint agents, which are used to output physical stimulation of laser light to patient's head acupoints; some of the acupoint agents are adjustably set on the acupoint setting base at a center of the top area to correspond to the Baihui acupoint and four Sishencong acupoints of the patient; one of the acupoint agents is configured to be positioned at the acupoint setting base in a position-adjustable manner at 10.35 centimeters forward from the center of the top area, corresponding to the Shenting acupoint of the patient; two of the acupoint agents are configured to be positioned at the back-side portion in a position-adjustable manner and located at the center of the top area by seven times a finger distance backward, and are separated by 5.175 centimeters in a direction toward the ear portions to respectively correspond to two Fengchi acupoints of the patient;

a phototherapeutic unit that includes two near-infrared light lamp groups for emitting low-energy near-infrared light, wherein one of the two near-infrared light lamp groups is arranged on the acupoint setting base and surrounds the Baihui acupoint of the patient, wherein the other of the two near-infrared light lamp groups is disposed on the acupoint setting base and surrounds the one of the acupoint agents corresponding to the Shenting acupoint of the patient;

an electronic stimulation unit that includes a first setting base and a second setting base that are respectively arranged in the side areas, and two electrical stimulation agents that are respectively arranged in the first setting base and the second setting base, the two electrical stimulation agents are used to output physical stimulation to the head of the patient, and the two electrical stimulation agents are configured to be positioned respectively in the F3 position and the F4 position of the international 10-20 system of electrode placement;

a display and optical frequency-flashed stimulation unit that is arranged on the supporting unit and is configured to be switched between a display mode and an optical frequency-flashed stimulation mode, wherein during the display mode, the display and optical frequency-flashed stimulation unit displays a virtual image for the patient's two eyes to watch, and wherein in the optical frequency-flashed stimulation mode, the display and optical frequency-flashed stimulation unit stimulates the patient's two eyes with a flashing light, the flashing light displayed by the display and optical frequency-flashed stimulation unit blinks at a predetermined frequency, and the predetermined frequency is between 35 Hz and 45 Hz, the display and optical frequency-flashed stimulation unit is a virtual image manipulation device, and includes a display module and an operation button;

a control unit that is electrically connected to the loudspeakers, the acupoint agents, the two near-infrared light lamp groups, the two electrical stimulation agents, and the display and optical frequency-flashed stimulation unit, and stores digital information of the binaural beats, and according to a preset command, simultaneously controls the loudspeakers to broadcast the binaural beats, the acupoint agents to emit physical stimulation, the two near-infrared light groups to emit near-infrared light, the two electrical stimulation agents to emit physical stimulation, and the display and optical frequency-flashed stimulation unit to switch modes;

wherein the control unit executes an assessment program, in which the control unit controls the display module to sequentially display evaluating cognitive impairment self-assessment questions, each cognitive impairment self-assessment question has self-assessment options, and a selected one of the self-assessment options is configured to be changed by changing a direction of the display module, after confirmation through the operation button, a cognitive self-assessment score corresponding to the selected one of the self-assessment options is generated and stored, and after all the cognitive impairment self-assessment questions are answered, a cognitive result score is generated and stored after adding up all the cognitive self-assessment scores.

2. The rehabilitation assistant system for a patient with cognitive impairments according to claim 1, wherein the wavelengths of the light emitted by the two near-infrared light groups are between 760 and 860 nm.

3. The rehabilitation assistant system for a patient with cognitive impairments according to claim 1, wherein, when the display and optical frequency-flashed stimulation unit is in the optical frequency-flashed stimulation mode, the flashing light displayed by the display and optical frequency-flashed stimulation unit respectively stimulates the eyes of the patient with different optical flash frequencies.

4. The rehabilitation assistant system for a patient with cognitive impairments according to claim 1, wherein an audio frequency difference of the binaural beats is between 0.1 Hz and 45 Hz, a wavelength of the laser light of the acupoint agents ranges from 500 nm to 900 nm, and an output power of the laser light ranges from 100 MW to 200 MW.

5. The rehabilitation assistant system for a patient with cognitive impairments according to claim 1, wherein when the two electrical stimulation agents are in a form of direct current output, a current size is between 0.5 mA and 2 mA, and a current density is between 0.03 $mA/cm^2$ and 0.09 $mA/cm^2$, and when the two electrical stimulation agents are in a form of transcranial magnetic stimulation, an electromagnetic frequency is between 1 Hz-20 Hz.

6. The rehabilitation assistant system for a patient with cognitive impairments according to claim 1, wherein each electrical stimulation agent has conductive pillars arranged in parallel to output physical stimulation.

7. The rehabilitation assistant system for a patient with cognitive impairments according to claim 1, that further includes an exercise unit, and the exercise unit is connected to the control unit by a signal for the patient to operate to exercise.

8. The rehabilitation assistant system for a patient with cognitive impairments according to claim 7, wherein the exercise unit includes an exercise bike, and the exercise bike has a frame, a crank rotatably arranged on the frame, two pedals arranged on opposite sides of the crank, a handle frame and a seat disposed on the frame, and the crank is also signally connected to the control unit to output a torque measuring signal corresponding to the torque sensor for measuring a torque of the crank.

9. The rehabilitation assistant system for a patient with cognitive impairments according to claim 1, wherein, the digital information and the preset command are downloaded through a cloud network and pre-stored in the control unit.

10. A rehabilitation assistant system for a patient with cognitive impairments, which is used by the patient, wherein the system includes:

a supporting unit that corresponds to a head shape of the patient, and that includes two ear portions corresponding to both ears of the patient, a top-side portion that spans a top of a head of the patient upward, a back-side portion that is connected between the ear portions and spans a back portion of a skull of the patient, a front-side portion connected between the ear portions and spanning a front portion of the skull of the patient, and the top-side portion has a top area located at a center of the ear portions, and two side areas respectively connected between the ear portions and the top area;

an audio stimulation unit that includes two loudspeakers arranged at the ear portions, and the loudspeakers are used to broadcast binaural beats to the both ears of the patient;

an acupoint stimulation unit that includes an acupoint setting base arranged in the top area, and acupoint agents, which are used to output physical stimulation of laser light to patient's head acupoints; some of the acupoint agents are adjustably set on the acupoint setting base at a center of the top area to correspond to the Baihui acupoint and four Sishencong acupoints of the patient; one of the acupoint agents is configured to be positioned at the acupoint setting base in a position-adjustable manner at 10.35 centimeters forward from the center of the top area, corresponding to the Shenting acupoint of the patient; two of the acupoint agents are configured to be positioned at the back-side portion in a position-adjustable manner and located at the center of the top area by seven times a finger distance backward, and are separated by 5.175 centimeters in a direction toward the ear portions to respectively correspond to two Fengchi acupoints of the patient;

a phototherapeutic unit that includes two near-infrared light lamp groups for emitting low-energy near-infrared light, wherein one of the two near-infrared light lamp groups is arranged on the acupoint setting base and surrounds the Baihui acupoint of the patient, wherein the other of the two near-infrared light lamp groups is disposed on the acupoint setting base and surrounds the one of the acupoint agents corresponding to the Shenting acupoint of the patient;

an electronic stimulation unit that includes a first setting base and a second setting base that are respectively arranged in the side areas, and two electrical stimulation agents that are respectively arranged in the first setting base and the second setting base, the two electrical stimulation agents are used to output physical stimulation to the head of the patient, and the two electrical stimulation agents are configured to be positioned respectively in the F3 position and the F4 position of the international 10-20 system of electrode placement;

a display and optical frequency-flashed stimulation unit that is arranged on the supporting unit and is configured to be switched between a display mode and an optical frequency-flashed stimulation mode, wherein during the display mode, the display and optical frequency-flashed stimulation unit displays a virtual image for the patient's two eyes to watch, and wherein in the optical frequency-flashed stimulation mode, the display and optical frequency-flashed stimulation unit stimulates the patient's two eyes with a flashing light;

a control unit that is electrically connected to the loudspeakers, the acupoint agents, the two near-infrared light lamp groups, the two electrical stimulation agents, and the display and optical frequency-flashed stimulation unit, and stores digital information of the binaural beats, and according to a preset command, simultaneously controls the loudspeakers to broadcast the binaural beats, the acupoint agents to emit physical stimulation, the two near-infrared light groups to emit near-infrared light, the two electrical stimulation agents to emit physical stimulation, and the display and optical frequency-flashed stimulation unit to switch modes;

wherein the supporting unit further includes two mounting slots respectively located in the side areas, and conductive strips are arranged at a bottom of the top-side portion, the first setting base has a first sliding member disposed under one of the side areas and the conductive strips, a first screw locking member that passes through the two mounting slots from a side opposite to the first sliding member of the top-side portion and is screwed to the first sliding member for fixing the first sliding member, a first positioning member of the first sliding member slidably passes through the first screw locking member from a side of the first screw locking member opposite to the first sliding member, a first mounting platform arranged on a side of the first sliding member opposite to the top-side portion and screwed to the first positioning member, and first conductive members telescopically passing through the first sliding member and the first mounting platform and electrically connecting the conductive strips, one of the two electrical stimulation agents is disposed on a side of the first mounting platform opposite to the top-side portion and electrically connected to the first conductive members, the second setting base has a second sliding member disposed under one of the side areas and the conductive strips, a second screw locking member passing through the two mounting slots from a side of the top-side portion opposite to the second sliding member and screwed to the second sliding member for fixing the second sliding member, a second positioning member of the second sliding member slidably passes through the second screw locking member from a side of the second screw locking member opposite to the second sliding member, a second mounting platform arranged on a side of the second sliding member opposite to the top-side portion and screwed to the second positioning member, and second conductive members telescopically passing through the second sliding member and the second mounting platform and electrically connecting the conductive strips, and the other of the two electrical stimulation agents is disposed on a side of the second mounting platform opposite to the top-side portion and electrically connected to the second conductive members.

* * * * *